(12) United States Patent
Bouchentouf

(10) Patent No.: US 8,840,852 B2
(45) Date of Patent: Sep. 23, 2014

(54) MULTI-POSITION SAMPLING VALVE

(75) Inventor: Olivier Bouchentouf, Montpellier (FR)

(73) Assignee: Horiba ABX SAS, Montpellier (FR)

( * ) Notice: Subject to any disclaimer, the term of this patent is extended or adjusted under 35 U.S.C. 154(b) by 529 days.

(21) Appl. No.: 12/746,566

(22) PCT Filed: Dec. 2, 2008

(86) PCT No.: PCT/FR2008/052174
§ 371 (c)(1),
(2), (4) Date: Sep. 21, 2010

(87) PCT Pub. No.: WO2009/077696
PCT Pub. Date: Jun. 25, 2009

(65) Prior Publication Data
US 2011/0281373 A1  Nov. 17, 2011

(30) Foreign Application Priority Data
Dec. 7, 2007  (FR) ...................................... 07 59631

(51) Int. Cl.
*G01N 1/10* (2006.01)
*G01N 1/18* (2006.01)
*G01N 35/10* (2006.01)

(52) U.S. Cl.
CPC .............. *G01N 1/18* (2013.01); *G01N 35/1097* (2013.01)

USPC .......................... 422/538; 436/180; 73/863.73

(58) Field of Classification Search
None
See application file for complete search history.

(56) References Cited

U.S. PATENT DOCUMENTS

| | | |
|---|---|---|
| 3,978,888 A | 9/1976 | Naono |
| 4,625,569 A | 12/1986 | Toei et al. |
| 4,948,565 A | 8/1990 | Bemis et al. |
| 5,255,568 A | 10/1993 | Del Valle et al. |
| 5,390,552 A | 2/1995 | Demachi et al. |
| 5,460,055 A | 10/1995 | Parker |
| 5,691,486 A | 11/1997 | Behringer et al. |
| 6,662,826 B1 | 12/2003 | Kokawa |

FOREIGN PATENT DOCUMENTS

| | | |
|---|---|---|
| EP | 0 220 430 | 5/1987 |
| EP | 0 545 560 | 6/1993 |
| FR | 2622692 | 5/1989 |

*Primary Examiner* — Robert Xu
(74) *Attorney, Agent, or Firm* — Clark & Brody

(57) ABSTRACT

The invention relates to a sampling valve, for taking samples of fluid from a common collecting vessel in order to perform a plurality of analyses using reagents. The valve of the invention comprises two members that are movable relative to each other, comprising a sampling member having sampling loops, each intended to receiving an aliquot of fluid, and a connection member capable of assuming at least three functional positions relative to the sampling member. These three positions enable the delayed access to two separate sampling circuits in order to fill them and to dispense reagents to the loops that make them up.

13 Claims, 8 Drawing Sheets

MULTI-POSITION SAMPLING VALVE

BACKGROUND OF THE INVENTION

The present invention relates to the general field of analyzing fluids. The invention applies more particularly to automatically analyzing fluids, whether biological fluids or otherwise.

In a particular application, the fluid is of human or animal origin. The invention is then particularly applicable to the field of analyzing blood. In this field, it is particularly useful to design systems and methods that perform such analyses in automatic manner.

In known systems and methods for performing hematological analyzes, total blood samples are generally taken directly from a patient, and then mixed with an anticoagulant. The initially-taken blood sample is then contained in a collecting vessel, usually a tube, optionally closed by a stopper. Conventionally these are said to be samples of total or complete blood.

Fluid analysis, in particular hematological analysis, generally requires a plurality of fractions of the total blood sample to be available. This makes it possible to perform a plurality of analyses or measurements on the same initial sample.

In the field of analyzing blood, known blood analyzers enable both different parameters to be measured and various elements constituting blood to be counted in order to obtain information about the state of health of patients. These parameters include in particular red and white corpuscles, hemoglobin, or indeed platelets.

It is then necessary for the initial sample to be divided into a plurality of fractions, referred to as aliquots. These aliquots are mixed with various reagents, and they are subjected to different treatments depending on the analyses that are desired.

Various systems and methods have been developed for taking blood from the collecting tube on one occasion only. This avoids the need to manipulate the tube several times with the attendant risk of contaminating the blood contained in the collecting tube. This also decreases the time the analyzer is occupied and increases the rate at which analyses can be performed, by releasing the collecting tube earlier.

In addition, known systems and methods generally enable the total volume taken on one occasion only to be smaller than would be possible if the blood sample were to be taken on several successive occasions.

Known systems and methods thus aliquot the blood before mixing it with various reagents and distributing it amongst various recovery and/or analysis means. The aliquots prepared with different reagents serve to determine values for the parameters of the sample, e.g. by means of optical measurement systems, thereby obtaining analysis results for all of the elements that constitute the blood.

Known systems and methods for fractioning the blood sample into multiple aliquots generally involve sampling valves that enable different aliquots to be taken on a single occasion and that enable them to be delivered on a plurality of occasions, so as to release the tube as quickly as possible. The aliquots present in the valve are then distributed to the same recovery and/or analysis means, one after another, or to different recovery and/or analysis means, optionally simultaneously.

More particularly, the invention thus relates to the field of sampling valves that enable a fluid to be sampled, in order to perform a plurality of analyses using various reagents.

French patent application FR 2 622 692, in the name of the Applicant, describes a so-called "linear" sampling valve in which a central moving member is sandwiched between two stationary members. It is necessary to rectify the faces of the members that are in friction contact with one another. That means it is necessary for four faces to be rectified in order to fabricate a valve in accordance with that document, so the cost of such a valve is high. In that valve, the movement of the moving portion defines a section in a channel present in the stationary portion connected to the moving portion. This section is subsequently isolated by moving the moving portion, and it corresponds to the volume of the aliquot that is to be used.

Other sampling valves also exist that are of a rotary type in which a member is movable in rotation between two stationary members.

By way of example, one such valve is described in U.S. Pat. No. 4,948,565 filed in the name of Fisher Scientific. Once more, it is necessary for four active faces to be rectified very accurately, thereby leading to high costs. The aliquots taken in a first position are subsequently dispensed to the measurement systems in a second position. Thereafter the entire system is rinsed in a third position. In the second position, it is not possible to separate at least some of the aliquots of blood from the reagents, and contamination may occur by liquid migration, in particular when certain analyses are not performed. The term "contamination" is used herein to mean the beginning of a reaction between an aliquot and a reagent, and also mixing between aliquots of two different samples. This makes it necessary to dispense new reagent to each loop as soon as it is in contact with the fluid for analysis, even if no analysis is to be performed subsequently. This leads to a wastage of reagent that is naturally economically harmful, and that is also often ecologically harmful.

U.S. Pat. No. 6,662,826 in the name of Abbott protects a four-member sampling valve. Fabricating such a valve requires six ceramic faces to be machined in order to achieve good operation, and that is extremely expensive. In addition, that valve does not enable distribution to be performed sequentially towards one or more recovery and/or analysis means. Once more, the blood aliquot is not physically isolated from the reagents and the taken sample may become contaminated.

U.S. Pat. No. 5,390,552, filed by Toa Medical Electronics, describes a valve made up of three members, two of which are stationary and one movable. That valve thus presents the same drawbacks as the valves described above. In addition, that valve does not propose timed delivery to a single measurement appliance.

U.S. Pat. No. 5,255,568, filed by Coulter Corporation, describes a valve having three members, two of which are stationary, and the middle third member is movable. Once more, it is necessary to machine four faces very accurately in order to obtain good results. There is still no possibility of timing the delivery of aliquots. Finally, in that patent, the valve can take only two positions, the first corresponding to sucking in aliquots and to rinsing the loops, and the second corresponding to dispensing reagents. Once more, the aliquots of blood and the reagents cannot be separated physically, and contamination may occur with migration taking place between the blood and the reagents.

All of those valves also present the drawback of limited access to the inside of the parts in order to clean them. When the orifices need to be purged, disassembly is not easy. Furthermore, when reassembling the valve, it is necessary to ensure that movements between the movable and stationary parts are very accurately adjusted. The large number of members constituting those valves thus constitutes a drawback.

OBJECT AND SUMMARY OF THE INVENTION

A main object of the present invention is thus to mitigate all of the drawbacks presented by prior art sampling valves, by proposing a sampling valve that makes it possible, from a single collecting vessel, to sample a fluid for a plurality of analyses using reagents, said valve comprising two members in contact with each other via respective ones of their faces referred to as "contact" faces, the two members being movable relative to each other, each member having a network of fluid-flow channels, at least some of which open out into the contact face thereof, wherein the network of channels of one of said members, referred to as a so-called sampling member, comprises at least three independent sampling loops, each suitable for containing an aliquot of the fluid, the sampling valve having at least as many reagent-dispenser channels and aliquot-outlet channels as it has loops, the other member, referred to as a so-called connection member, being capable of taking at least three distinct functional positions relative to the sampling member:

- a first position enabling a fluid inlet into the valve to be connected to a first sampling circuit comprising a plurality of sampling loops that are then connected to one another via channels of the network of channels of the connection member that are then specifically in alignment with each of the loops, said first position also serving to connect, via one or more channels of the network of channels of the connection member, at least one loop of a second sampling circuit, having at least one sampling loop, to a reagent-dispenser channel and to an aliquot-outlet channel;
- a second position enabling the fluid inlet to be connected to the second sampling circuit; and at least
- a third position in which at least one sampling loop of the first circuit is connected via channels of the network of channels of the connection member to a reagent-dispenser channel and to an aliquot-outlet channel.

It should be understood that the hardware element referred to by the term "sampling circuit" as being capable of including one or more sampling loops in which, as soon as at least two sampling loops are included in the circuit, said loops are connected together by aligning the loops with the network of channels of the connection member when the fluid inlet is connected to said sampling circuit.

The proposed sampling valve enables different aliquots to be taken and then distributed at different times, thereby enabling the collecting tubes to be released as quickly as possible. In addition, it presents the advantage of enabling the blood aliquots and the reagents to be isolated, so as to avoid contamination.

With the sampling valve of the invention, the aliquots present in the valve may be delivered over a common measurement channel, one after another, or over a plurality of different measurement channels. The use of a sampling valve of the invention thus makes it possible to fraction the initially-taken sample into a plurality of aliquots of determined volumes and subsequently to deliver them simultaneously or sequentially into containers of the analysis system, which is very practical. The valve of the invention thus enables injection to be deferred/delayed over time, thereby making it possible for an injection to depend on the analysis results from the first aliquot to be analyzed.

It is then possible to achieve very high rates of throughput, even while performing a plurality of different analyses. In particular, using two sampling circuits, each having a plurality of sampling loops, makes it possible for certain operations to be performed on one of the sampling circuits while other operations are being performed on the second sampling circuit. Thus, where prior art solutions propose two positions, the invention proposes at least three, each of which has a function that is useful and original.

These three positions give deferred access to two separate sampling circuits in order to fill them and in order to dispense reagents into the loops making them up.

The invention thus makes it possible to rinse the first sampling circuit while simultaneously dispensing reagent to the second sampling circuit. The invention thus makes it possible to use only one of the first and second sampling circuits, thereby conserving the isolation of the sampling loops of the non-used sampling circuit from the reagents. This makes it possible to economize reagents if it is desired to perform the analysis(es) of only one of the circuits. The device thus makes it possible to consume only the quantity of reagent(s) that is strictly necessary for the analysis undertaken.

Thus, using a common position for two distinct functions in the first sampling circuit and the second sampling circuit enables time to be saved in the analysis process.

It should be observed at this point that the loops may be identical or different in size. It is thus possible to vary dilution by using valves having loops of varying lengths depending on requirements. It is also possible to modify dilutions by modifying reagent volumes.

In a first implementation of the invention, in the third position, all of the loops of the first circuit are each connected, via channels of the network of channels of the connection member, to a respective reagent-dispenser channel and to a respective aliquot-outlet channel.

This implementation enables reagents to be dispensed to all of the loops of the first sampling circuit in parallel, thereby contributing to reducing analysis, durations very considerably. Nevertheless, that presents the drawback of putting reagent into contact with the aliquot even if the analysis of one particular sampling loop is not performed. This embodiment is particularly appropriate when all of the analyses of the first sampling circuit are certain to be performed in any event. The analyses that are not performed on each occasion are performed using the second sampling circuit that may optionally be made up of a plurality of loops, at least one of which, or a fraction of which, or indeed all of which, may have reagent dispensed therein while the valve is in the first position.

In a second implementation, the connection member is designed to take a third position such that a fraction only of the sampling loops of the first circuit are each connected, via channels of the network of channels of the connection member, to a respective reagent-dispenser channel and to a respective aliquot-outlet channel, and to take at least one other functional position such that at least one other distinct fraction of the sampling loops of the first circuit are each connected, via channels of the network of channels of the connection member, to a respective reagent-dispenser channel and to a respective aliquot-outlet channel.

When at least one of the sampling loop fractions comprises a plurality of loops, this implementation serves to avoid polluting the reagents when dispensing them to the plurality of loops of the first circuit, while guaranteeing the ability to perform a plurality of analyses simultaneously.

Each of the sampling loop fractions may be constituted by a pair of sampling loops. Each may also be constituted by a single sampling loop.

When using single loops, the advantage of being able to dispense reagent to a plurality of loops in the first circuit simultaneously is lost, but the dispensing of reagents can be totally dissociated. Nevertheless, in this implementation, the invention still enables the first circuit to be filled, while simultaneously dispensing reagent to a loop of the second circuit. There is thus still a saving of time.

In a first particularly advantageous preferred embodiment, the connection member is also a dispenser member carrying the reagent-dispenser channels and the aliquot-outlet channels of the sampling valve.

In a second preferred embodiment, the sampling member is also a dispenser member carrying the reagent-dispenser channels and the aliquot-outlet channels of the sampling valve.

The multiposition sampling valve then integrates all of its functions using only two hardware members. It contains fewer members than prior art sampling valves while enabling more functions to be performed. It is also easier to disassemble for maintenance, and overall it is less subject to wear and less expensive to machine. Finally, since the valve is simpler to make, any risks of leaks between the parts are reduced.

Finally, in these preferred embodiments, construction of the valve is greatly simplified, since the connection (or sampling) member carries both the connection channels (or the sampling loops) and the dispenser channels.

In an advantageous embodiment, the members are disks that are movable in rotation relative to each other.

Such an embodiment enables a very compact valve to be constructed, with rotary movement being particularly suitable for bringing the channels carried by the various members into alignment.

Preferably, the connection member carries a channel constituting the fluid inlet to the valve.

This characteristic makes it possible for the sampling valve of the invention to be particularly simple to make, and it ensures that the assembly is compact, while also ensuring that the valve is very simple to make with two members. This also ensures good accessibility to the inlet of the valve.

Nevertheless, the inlet may also be a channel carried by the sampling member and connected as required to the sampling circuit via the connection member.

In an advantageous application of the invention, with the fluid being a biological fluid, the first circuit is dedicated to systematic analyses while the second circuit is dedicated to analyses that are not systematic.

Whereas sampling valves of the prior art have required as many sampling loops to be provided as there are systematic analyses and non-systematic analyses that can be performed by the same sampling valve, given that all of the sampling loops have reagent dispensed thereto in the same position of the valve, the invention makes it possible to dispense reagent to each of its two sampling circuits independently. The first circuit then advantageously comprises the sampling loops for performing systematic routine analyses, and the second circuit comprises sampling loops for performing non-systematic routine analyses.

Since the invention makes it possible to dispense reagent to these two circuits in deferred manner, reagent contamination for the particular analyses is avoided, even when all of the routine analyses are performed.

A very high rate of throughput is then made possible, since it is possible to avoid dispensing reagent to one or more loops without requiring the loops to be cleaned because of possible contamination with reagents. This advantage is in addition to the fact that it is possible to perform two distinct operations on the first and second sampling circuits while the valve is in a single position.

The invention also provides an analysis appliance using the sampling valve, and a method of sampling a fluid that is implemented in an analysis appliance of the invention using a sampling valve of the invention.

Such a method comprises the following steps:
taking up the first position;
filling the first sampling circuit by sucking fluid placed in the collecting vessel towards the valve inlet;
taking up the second position;
filling the second sampling circuit by sucking fluid placed in the collecting vessel towards the valve inlet;
taking up the third position;
dispensing reagents over at least one loop of the first sampling circuit towards one or more analysis means;
taking up the first position;
dispensing reagents over at least the loop of the second sampling circuit to one or more sampling means;
rinsing the first sampling circuit by sucking in a rinsing fluid placed in a rinsing container, it being possible to perform this step before, after, or simultaneously with the preceding step;
taking up the second position; and
rinsing the second sampling circuit by sucking in a rinsing fluid placed in a rinsing container.

BRIEF DESCRIPTION OF THE DRAWINGS

Other characteristics and advantages of the present invention appear better on reading the following description made by way of non-limiting illustration and with reference to the accompanying drawings, in which.

DETAILED DESCRIPTION OF AN EMBODIMENT

Figure 1A:
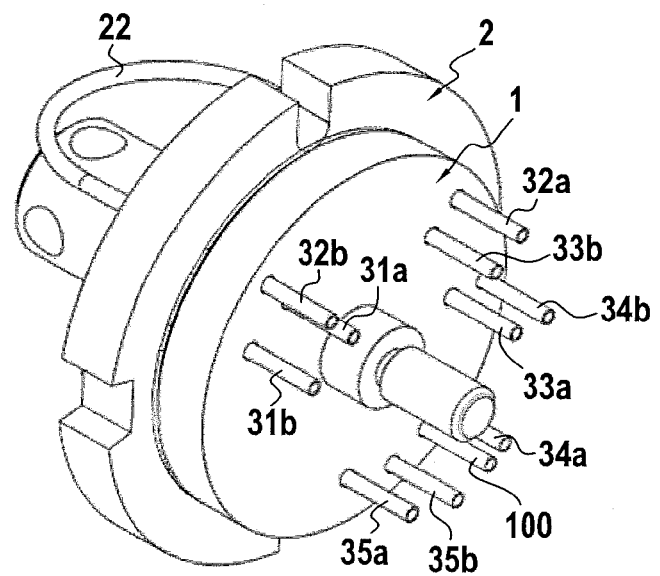
FIGS. 1A and 1B are perspective views of a sampling valve in a preferred embodiment of the invention.
Figure 1B:
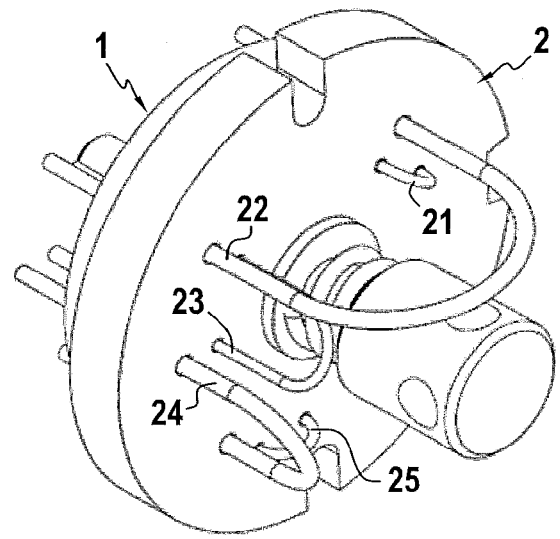

FIGS. 1A and 1B are perspective views of a preferred embodiment of a sampling valve of the invention. The valve is constituted by a connection member 1 and a sampling member 2. These two members 1 and 2 are both disks that are in contact with each other via two respective faces 10 and 20. The connection member 1 is mounted to turn relative to the sampling member 2, with such turning being represented diagrammatically by a double-headed arrow.

In the preferred embodiment of FIG. 1, the connection member 1 has an inlet 100 for the fluid for analysis. When the valve is in operation, this inlet 100 of the sampling valve is connected to a collecting tube by appropriate means. Advantageously, the inlet 100 is not connected to a tube, but is connected to a needle having its own mode of insertion and known as a spike. The spike enables the inlet 100 to be connected to the collecting tube. In this embodiment, the connection member 1 also includes channels 31*a* & 31*b*, 32*a* & 32*b*, 33*a* & 33*b*, 34*a* & 34*b*, 35*a* & 35*b* for dispensing and removing reagents.

The sampling member 2 has a certain number of sampling loops 21, 22, 23, 24, and 25, and a fluid outlet 200 that is not visible in FIGS. 1A and 1B.

Figure 2A:
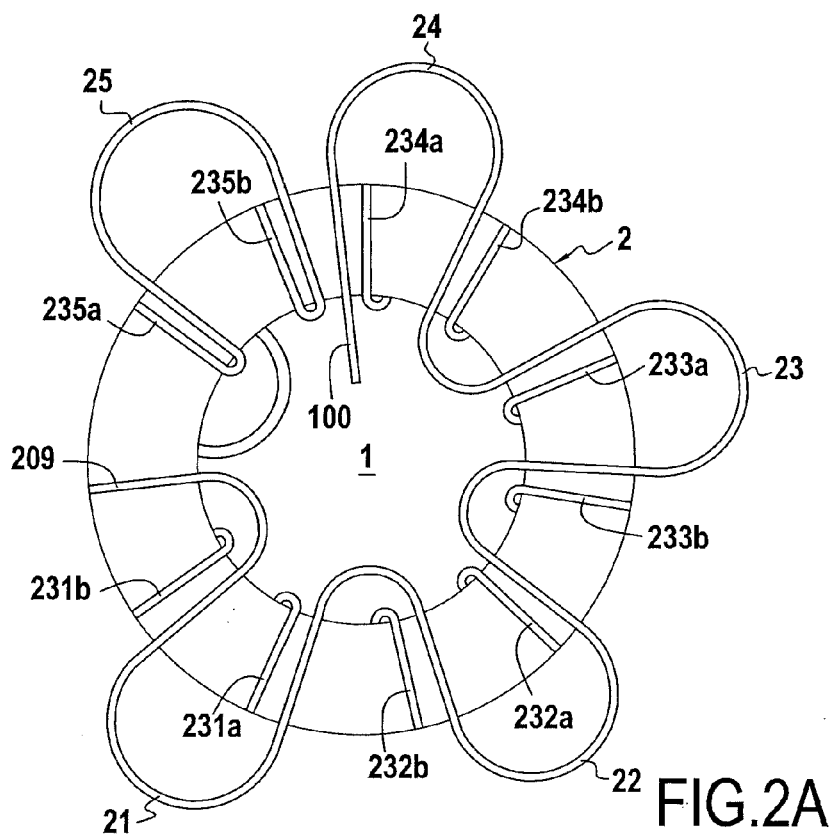
FIGS. 2A and 2B are respectively a diagrammatic representation of the multiposition sampling valve of the invention suitable for explaining the operation thereof, and an enlargement of the connection member as shown diagrammatically in FIG. 2A.
Figure 2B:
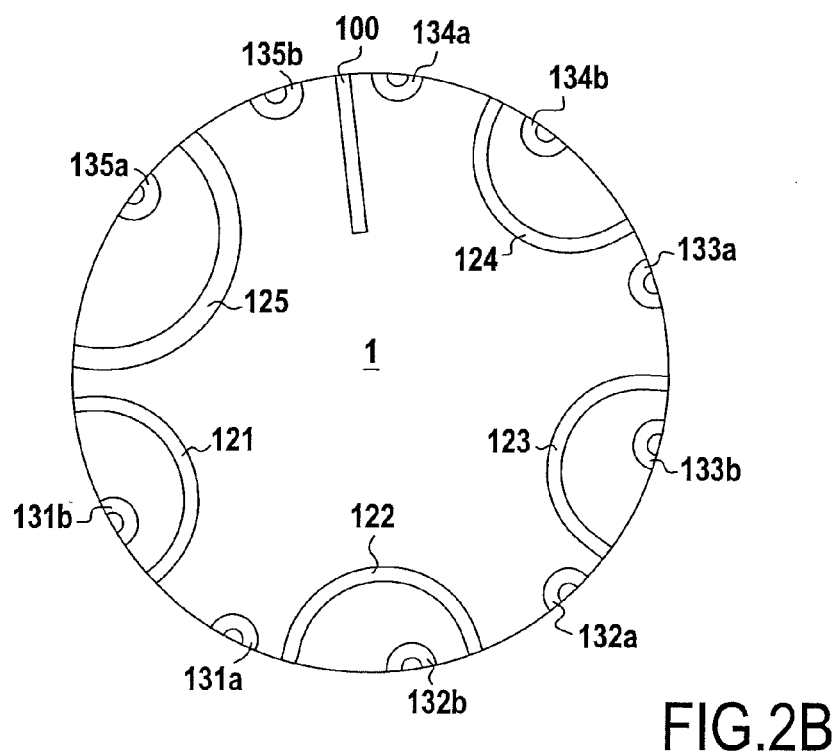

The sampling valve in the preferred embodiment of FIGS. 1A and 1B is also shown diagrammatically in FIGS. 2A and 2B. This diagrammatic representation makes it easier to understand the operation of the sampling valve.

In this representation, the channels of the connection member 1 and the sampling members 2 are shown as lying in a common plane.

The connection member 1 is then represented in the form of a central disk, while the sampling member 2 is represented in the form of a ring surrounding the central disk, i.e. the connection member 1, which disk is movable in rotation relative to the ring, i.e. the sampling member 2.

The connection member 1 is for interconnecting certain channels of the sampling member 2. The interconnections shown are those of a preferred implementation of the invention.

FIG. 2B shows the connection member 1 on its own, in the same diagrammatic representation as FIG. 2A. It includes the inlet 100 and channels 121, 122, 123, 124, and 125 for establishing fluid flow connection between certain channels of the sampling members.

The ring, i.e. the sampling member 2, carries the sampling loops 21, 22, 23, 24, and 25. In order to simplify the representation, the channels 31*a* & 31*b*, 32*a* & 32*b*, 33*a* & 33*b*, 34*a* & 34*b*, 35*a* & 35*b* for dispensing and removing reagents are shared diagrammatically between the two members 1 and 2, whereas in the preferred embodiment of FIG. 1, they are carried solely by the connection member 1.

Each channel 3X*a* or 3X*b*, where X=1 to 5, is then represented in FIGS. 2A and 2B by two channels 13X*a* and 23X*b* carried respectively by the connection member 1 and the sampling member 2. These two channels 13X*a* and 23X*b* are such that they are in alignment with each other and in alignment with a sampling loop 2X when the valve is in a dispensing position on one or more sampling loops, as explained below.

Here it should be observed that, in another embodiment of the invention, these dispenser and removal channels carried by the connection member 1 in FIG. 1 may advantageously be carried equally well by the sampling member 2. Such an embodiment still conserves the advantage of having only two members that are movable relative to each other.

In the preferred embodiment of FIG. 1 shown diagrammatically in FIG. 2, the sampling valve carries two separate sampling circuits. The first sampling circuit is constituted by the loops 21, 22, 23, and 24, while the second sampling circuit comprises the loop 25 only.

FIGS. 3A to 3E illustrate the operation of the sampling valve. The sampling valve is in a first position in FIG. 3A, corresponding to the position shown in FIG. 2.

In this first position, the loop 24 is connected to the inlet 100 of the valve, the loop 24 is connected to the loop 23, itself connected to the loop 22, itself connected to the loop 21, itself connected to the outlet 200 carried by the sampling member 2. More particularly, in this first position, the loop 24 and the loop 23 are connected together via the channel 124 of the connection member 1. The loop 23 is connected to the loop 22 via the channel 123 of the connection member 1, the sampling loop 22 is connected to the loop 21 via the channel 122 of the connection member 1, and finally the loop 21 is then connected to the outlet 200 of the sampling valve by the loop 121 of the connection member.

In parallel, it can be seen that the loop 25 is then connected to two channels, one for dispensing and another for removing the aliquot, which channels are constituted by the channels 135*a* & 135*b* and 235*a* & 235*b* of FIGS. 2A and 2B.

It can readily be understood that the arrangement of the channels on the connection member 1 complies precisely with the function of the invention of being able to connect a first sampling circuit to a fluid inlet while a second sampling circuit is connected to elements for dispensing reagent and for removing the aliquot.

Figure 3A:
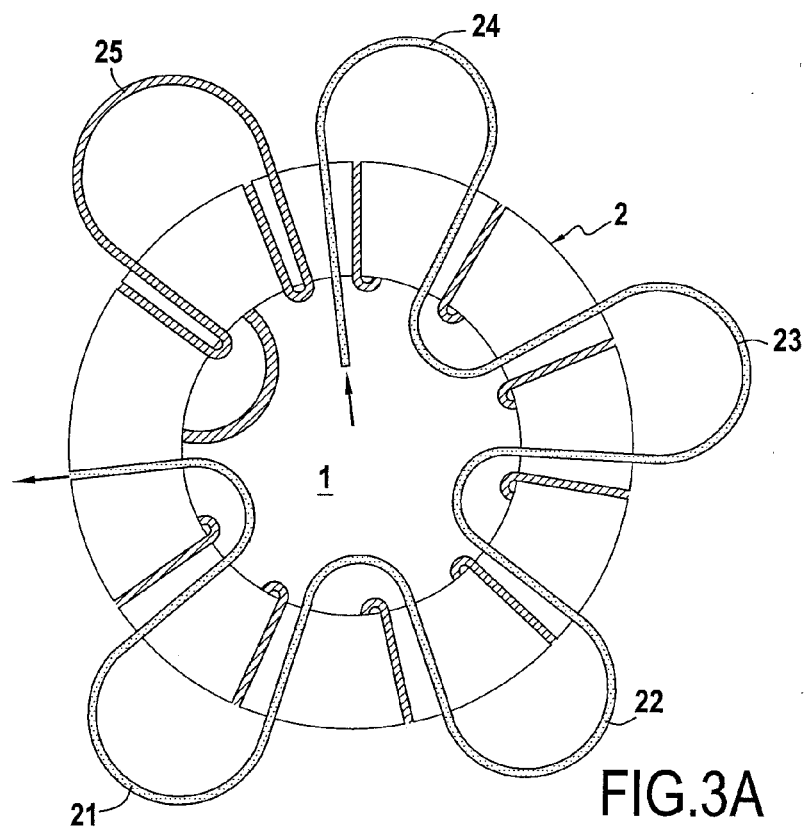
FIGS. 3A to 3E illustrate the operation of the multiposition sampling valve in a preferred implementation of the invention, using the diagrammatic representation of FIGS. 2A and 2B.

In FIG. 3A, the first sampling circuit is filled with a fluid for analysis taken and sucked into the valve via the inlet 100. This blood is represented by dots. The other channels in FIG. 3A are filled with another fluid, e.g. a rinsing fluid, represented by shading.

Figure 3B:
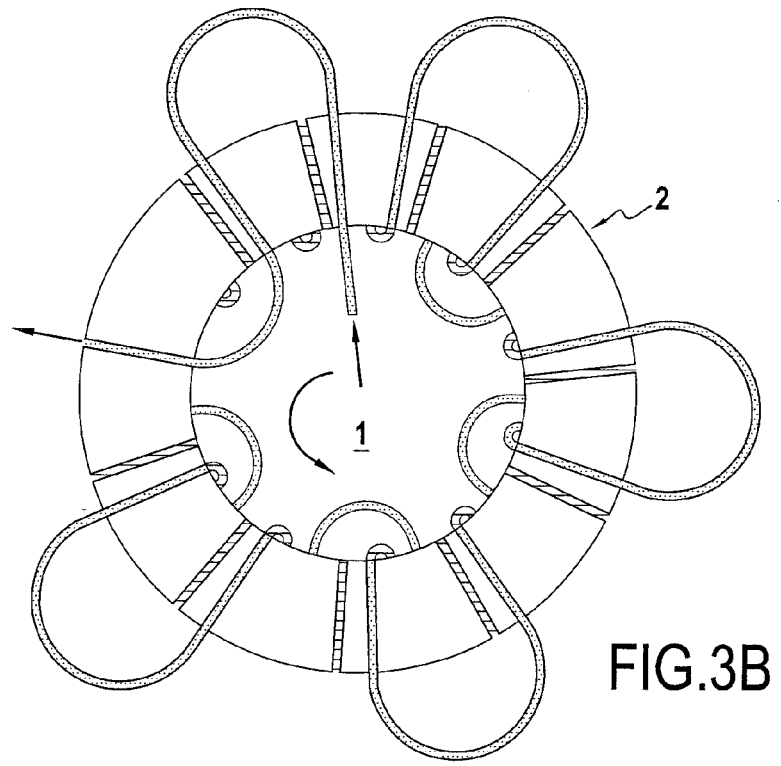

FIG. 3B shows the sampling valve in a second position in which the inlet 100 of the sampling valve is in alignment with the loop 25 that constitutes the second sampling circuit in the preferred embodiment of FIG. 1. The loop 25 is then also connected to the outlet 200 via a channel 125 of the connection member 1. This second member enables the second sampling circuit to be filled with the blood sucked in through the inlet 100.

It should be observed at this point that the second circuit could very well have a plurality of sampling loops, providing the distribution of the loops on the sampling member 2 is made more compact and providing the connection member is given channels suitable for connecting the various loops together in the same manner as the four loops of the first sampling circuit are connected together.

During this time, the aliquots present in each of the loops of the first sampling circuit are isolated from one another and they are isolated from the aliquot dispenser and removal channels where there might be reagents.

Figure 3C:
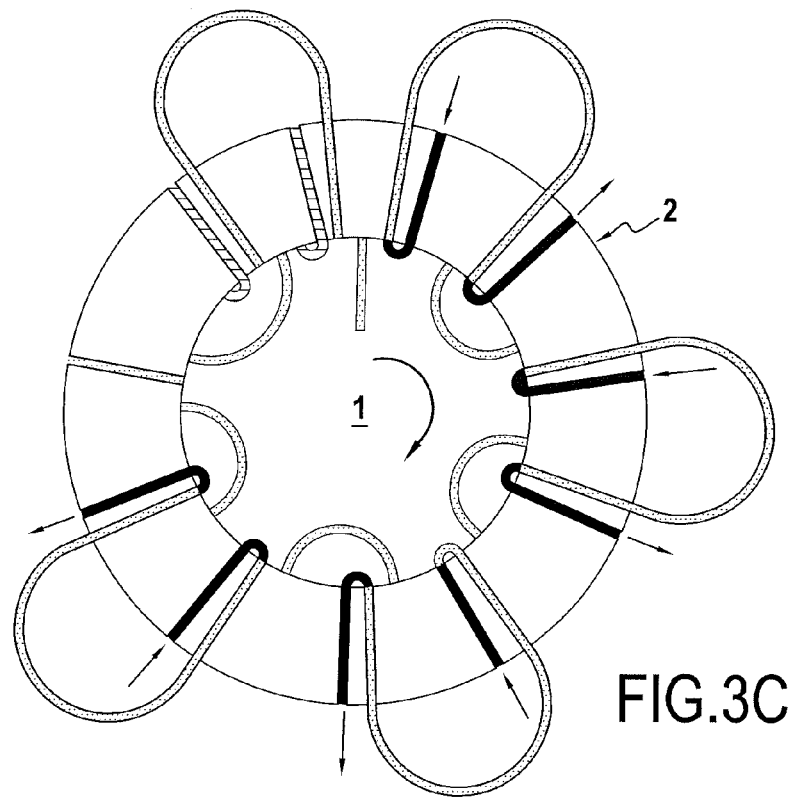

In FIG. 3C, the connection member takes a third position in which the inlet 100 is isolated from all of the sampling loops of the valve. At this moment, the collecting tube may be released. It is explained below that it could also be removed earlier in a variant embodiment.

It can be seen that in the third position the loop 25 of the second sampling circuit is isolated from all of the channels. It therefore runs no risk of being contaminated.

In contrast, in the preferred implementation shown in FIG. 3, each of the loops 21, 22, 23, and 24 of the first sampling circuit is connected to a reagent dispenser circuit and to an aliquot removal circuit that is specific thereto.

Thus, one end of the sampling loop 21 is connected to a reagent-dispenser channel constituted by the channel 131*a* of the connection member 1 and the channel 231*a* of the sampling member 2, whereas the other end of the sampling loop is connected to an aliquot removal channel constituted by the channel 131*b* carried by the connection 1 and by the channel 231*b* carried by the sampling member 2.

Similarly, the sampling loop 22 is connected at one end to a reagent-dispenser channel constituted by the channel 132*a* of the connection member 1 and the channel 232*a* of the sampling member 2, while the other end of the sampling loop is connected to an aliquot removal channel constituted by the channel 132*b* carried by the connection member 1 and the channel 232*b* carried by the sampling member 2.

The same applies respectively to the reaction loops 23 and 24 put into communication with the reagent-dispenser channels respectively constituted by the channels 133a, 233a and 134a, 234a, and the aliquot removal channels constituted by the channels 133b, 233b and 134b, 234b.

In this third position, reagent is dispensed into each of the loops 21, 22, 23, and 24. The blood aliquots mixed with the respective reagents are conventionally recovered in one or more analysis appliances (not shown). This or these appliance (s) serve(s) to perform analyses that may be simultaneous or sequential, identical, partially distinct, or completely distinct.

Thus, for a given fluid, up to four types of analysis may be performed simultaneously in one or more analysis appliances suitable for implementing them.

It is also possible to envisage the aliquots being sent sequentially to the same analysis device, each loop having a distinct reagent dispensed therein and seeking to evaluate some particular parameter that is suitable for being measured by identical analysis means.

In general, it is necessary to pause for a certain length of time, a few seconds, e.g. 30 seconds, once the reagents have been dispensed in order to allow for reaction kinetics in the aliquots. In this third position, it is advantageously observed that there can be no contamination between a reagent and any blood aliquot, here the aliquot in the loop 25.

Figure 3D:
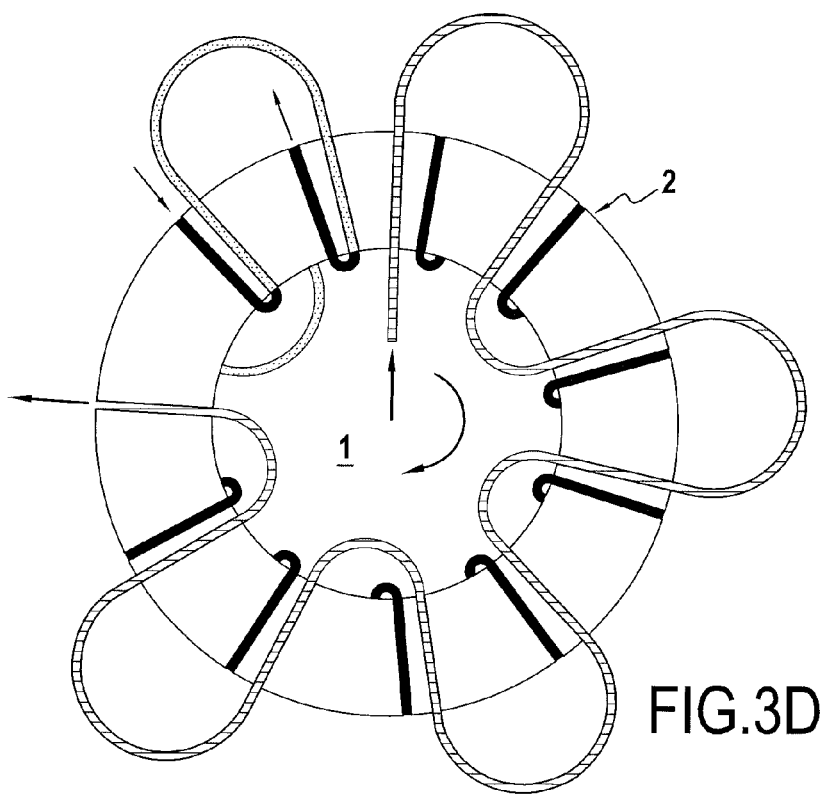

During the pause, as shown in FIG. 3D, the connection member 1 may advantageously be moved so as to return to the first position. Since the loops 21 to 24 are connected to one another, this enables the loops of the first sampling circuit 21, 22, 23, and 24 to be cleaned by sending the rinsing liquid thereto.

Simultaneously, since the loop 25 is then connected to the dispenser and removal channels, the first position makes it possible to dispense the last aliquot contained in the loop 25 towards suitable recovery and/or analysis means that may optionally be different from the analysis means used for one or more of the loops of the first circuit.

The cleaning of the loops 21 to 24 and the dispensing from the loop 25 are thus performed simultaneously, thereby making a considerable time saving possible. More generally, with the invention, since certain distinct functions are performed simultaneously for a first circuit and for a second circuit, this type of parallel working enables a very large amount of time to be saved when performing analyses.

It can be seen that in the implementation of the invention described herein, the second circuit has only one sampling loop and, at present, that is the most suitable for blood analysis applications. Nevertheless, the second circuit could have a plurality of sampling loops. Under such circumstances, at least one of them may have reagent dispensed thereto in the first position in the meaning of the invention, i.e. at the same time as the first circuit is connected to the fluid inlet. The other loops of the second circuit may have reagent dispensed thereto in the same said first position or in positions that are distinct from the first position.

In particular implementations of the invention, these other relative positions of the connection and sampling members enabling one or more loops of the second circuit to have reagent dispensed thereto may optionally also enable reagent to be dispensed simultaneously to one or more loops of the first circuit.

Figure 3E:
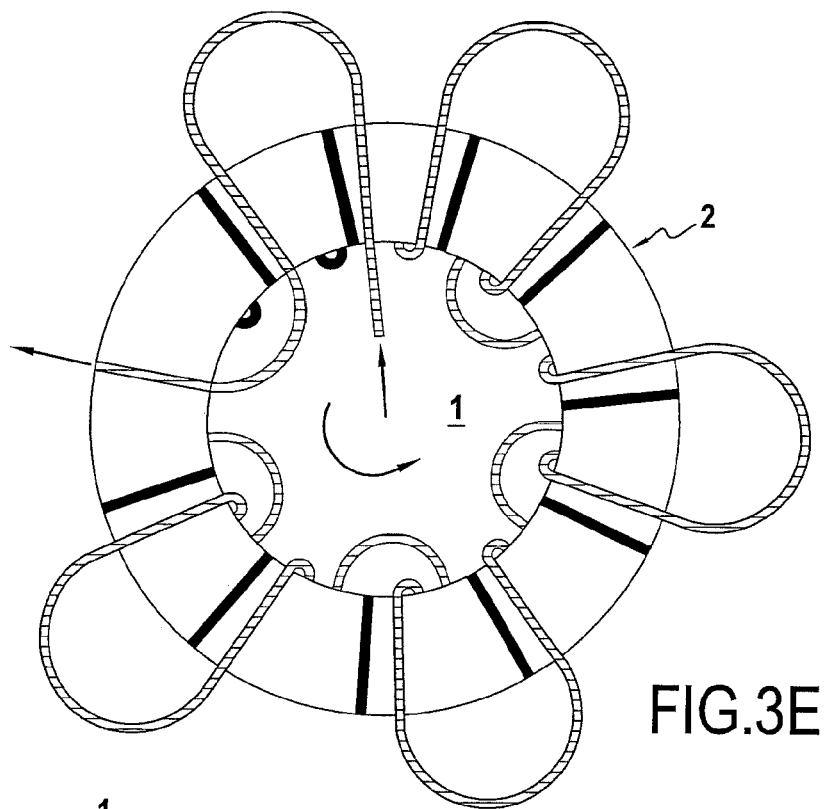

Finally, in FIG. 3E, with the help of the motor that turns the connection member 1, the connection member returns to the second position, thereby enabling the fifth loop 25 to be cleaned with the same rinsing liquid as the four first loops or using a different rinsing liquid.

The invention makes it possible to use different rinsing liquids for the two sampling circuits. This is particularly advantageous when the nature of some particular reagent, e.g. the reagent used in the loop 25, makes it necessary to clean it with a rinsing liquid that is different from that used for the four first loops 21 to 24.

At the end of the five-step cycle represented in FIGS. 3A to 3E, it is thus possible to perform five different analyses from the same initial blood sample taken once only from the tube.

It is possible to perform the analyses in two stages so that some are performed simultaneously and others in deferred manner.

It is thus possible to reduce the length of time the collecting tube is used by the machine, thus making it possible to increase rates of throughput while improving performance by having isolated aliquots.

It should also be observed that insofar as it is possible to perform deferred analyses, it is possible to condition the performance of some particular analysis as a function of the results of certain analyses that are performed beforehand.

In addition, the sampling valve system of the invention makes it possible to perform only a fraction of the analyses that are available using the sampling valve, by making use of only a fraction of the sampling circuits. The invention may be used to take a sample on only one of the two sampling circuits so as to perform only a fraction of the analyses, and thus take only the strictly necessary quantity of blood.

For example, it is possible to desire results only from the analysis of the fifth loop 25. By putting the valve in the second position, it is then possible to fill only the loop 25 which is completely separate from the remainder of the valve, and in particular from the first sampling circuit. Reagent is dispensed to the loop 25 is then performed by returning the sampling valve to the first position. Thereafter the loop 25 is rinsed merely by returning to the second position.

This is made possible without any modification to the valve or to the positions that the valve can take. To perform a single analysis only, it is therefore appropriate to take only one sample directly in the second position, without going via the first position.

Thus, the first sampling circuit does not come into contact with the sample of blood nor with any reagent, so there is no need to clean it. This makes it possible significantly to reduce the volumes of reagents and blood that are taken in order to perform a single analysis. It can be understood that the invention makes it possible to perform at least one analysis even if the blood sample is not of very large volume.

In identical manner, if it is desired to have the results from only the analyses of the four first loops, there is no need to fill the fifth loop.

When it is desired to perform the analyses of the four first loops, the valve is initially put into the first position so as to take the four aliquots needed, prior to passing directly to the third position that enables each of these aliquots to be dispensed to the appropriate recovery and/or analysis means. A return to the first position then enables the loops 21, 22, 23, and 24 to be cleaned.

In this example, the loop 25 does not come into contact with the blood sample nor with any reagent. There is therefore no need to clean this loop, thus likewise making it possible, as explained above, to reduce the volumes of reagent and the volumes of blood that are taken.

The invention envisages fractioning the number of loops in the first sampling circuit in manners that are different in terms of their possibilities for having reagents dispensed thereto.

FIG. 4 is a diagram showing such an implementation in which the loops of the first sampling circuit are suitable for having reagent dispensed thereto simultaneously in pairs. One of the reagent-dispensing positions is the second position of the invention, since it also enables the second sampling circuit to be filled.

Figure 4A:
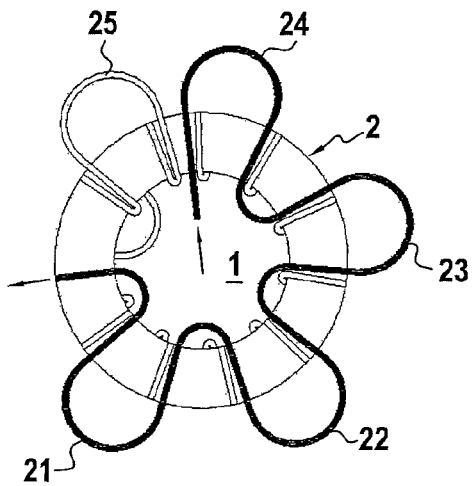
FIGS. 4A to 4E illustrate the operation of a valve in a particular implementation of the invention using the diagrammatic representation of FIGS. 2A and 2B.

In FIG. 4A, the valve is in the first position in which a first circuit constituted by loops 21, 22, 23, and 24 can be filled and the loop 25 can have reagent dispensed thereto, since it is connected to a reagent-dispenser channel and to an aliquot-outlet channel.

Figure 4B:
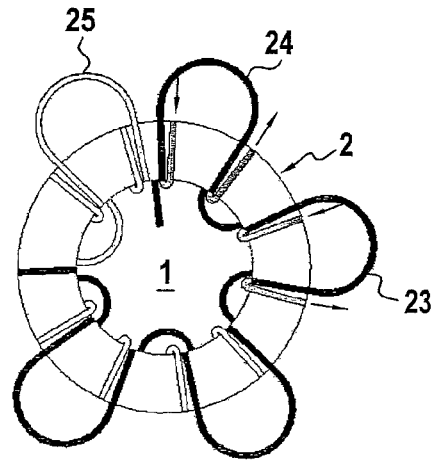

In FIG. 4B, the sampling valve is in a third position in the meaning of the invention and the two loops 23 and 24 are each connected to a respective reagent-dispenser channel and to a respective aliquot-outlet channel.

Figure 4C:
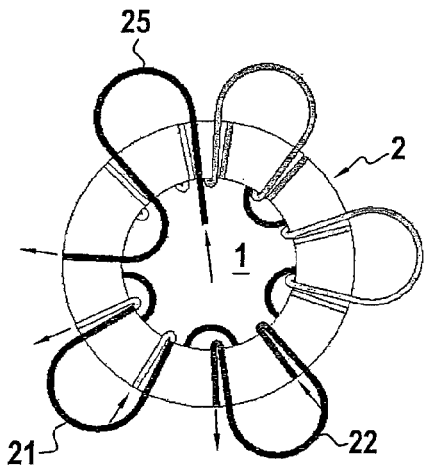

In FIG. 4C, the sampling valve is in a second position in the meaning of the invention, since in this position, the second circuit constituted by the loop 25 can be filled, at the same time as in a third position in the meaning of the invention, since the loops 21 and 22 are each connected to a respective reagent-dispenser channel and to a respective aliquot-outlet channel.

This position is another functional position, specifically a fourth functional position, combining the functions of the second and third positions of the invention. The resulting sampling valve, coming within the scope of claim 1, is protected more particularly by claim 4.

Figure 4D:
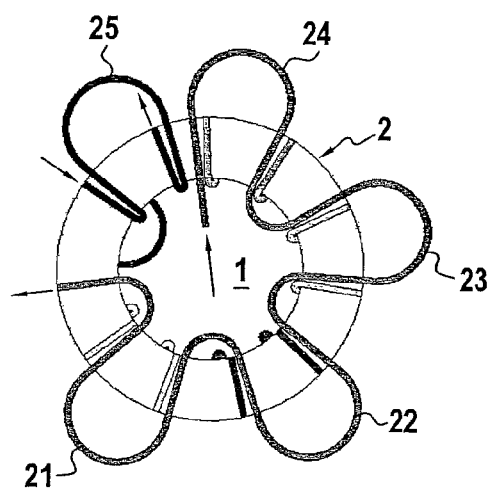
Figure 4E:
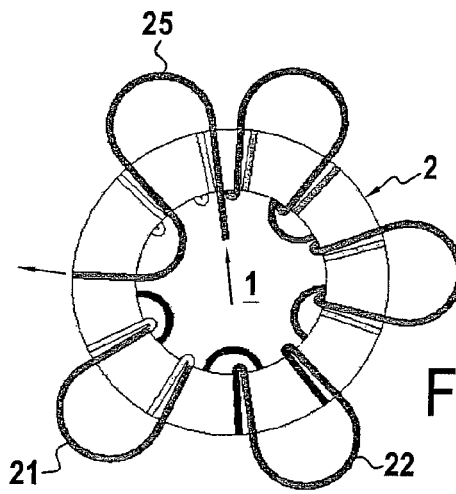

In FIG. 4D, the first sampling circuit may be rinsed while the second circuit, constituted by the loop 25 may have reagent dispensed thereto. In FIG. 4E, the loop 25 is rinsed. In this position, the loops 21 and 22 are each connected to a respective reagent-dispenser channel and to a respective aliquot-outlet channel, but that is not troublesome insofar as the loops 21 and 22 have been rinsed.

FIG. 5 shows another implementation with yet another type of fractioning of the number of loops in the first sampling circuit as to their possibilities for having reagent dispensed thereto.

Figure 5A:
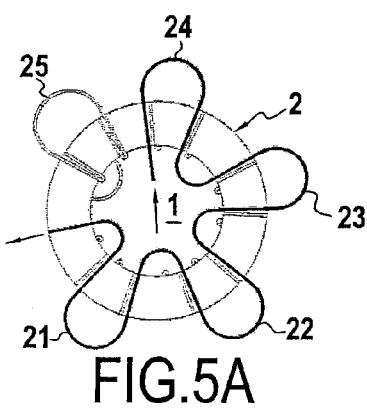
FIGS. 5A to 5H illustrate the operation of a valve in another particular implementation of the invention, still using the diagrammatic representation of FIGS. 2A and 2B.
Figure 5B:
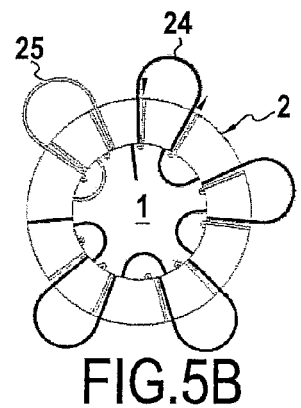
Figure 5C:
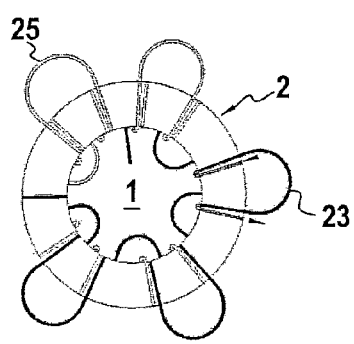
Figure 5D:
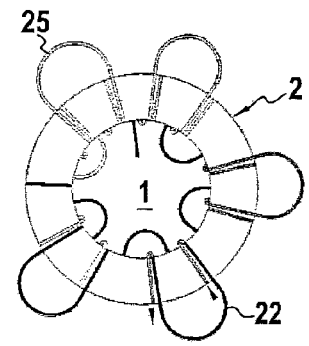
Figure 5E:
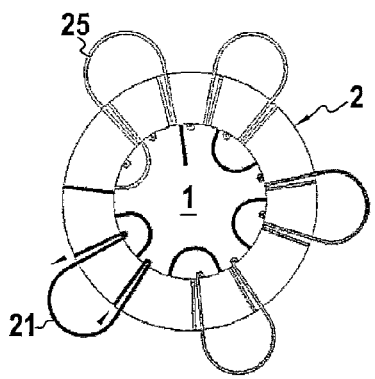

In this implementation, the loops 21, 22, 23, and 24 of the first sampling circuit are filled in the same position, shown in FIG. 5A, in which the loop 25 of the second circuit is connected to a reagent-dispenser channel and to an aliquot-outlet channel. This position is the first position in the meaning of the invention.

Thereafter, the distinct relative positions of the connection and sampling members shown respectively in FIGS. 5B, 5C, 5D, and 5E enable the loops 24, 23, 22, and 21 to be connected with respectively reagent-dispenser channels and with respective aliquot-outlet channels.

A distinct position in this example is used for each loop. There are thus as many "third" positions in the meaning of the invention as there are loops in the first circuit. When the second circuit is made up of a plurality of loops, some of these positions may also serve to connect one of the loops of the second circuit to a reagent-dispenser channel and to an aliquot-outlet channel.

Figure 5F:
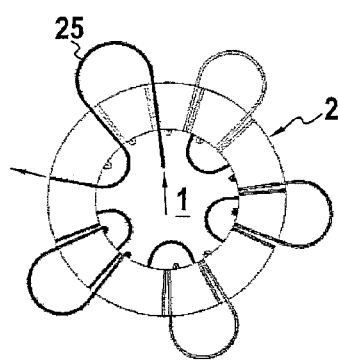
Figure 5G:
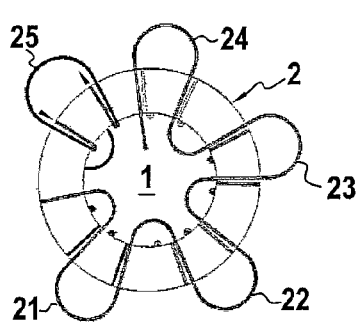
Figure 5H:
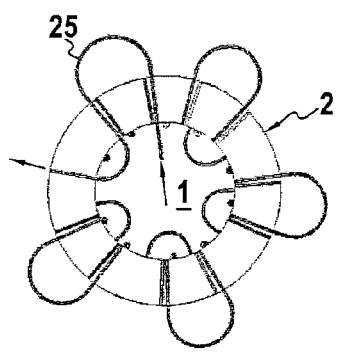

FIG. 5F shows the second position in the meaning of the invention in which the loop 25 can be filled. In FIG. 5G, the valve is in the same position as in FIG. 5A. The first circuit is then rinsed while the second circuit is having reagent dispensed thereto. Finally, in FIG. 5H, the second circuit is rinsed in the same position as shown in FIG. 5F that enables the inlet of the valve to be connected to the second circuit.

Figure 6:
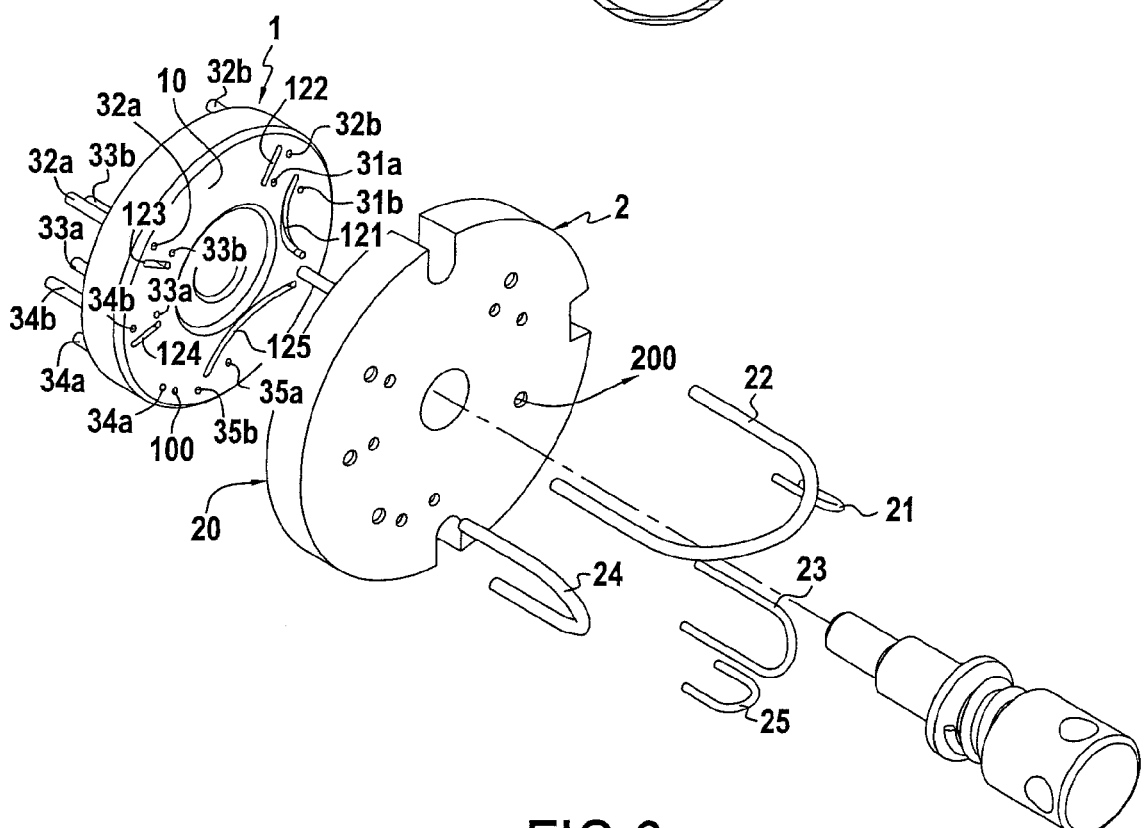
FIG. 6 is an exploded perspective view of the sampling valve as shown in FIGS. 1A and 1B.

FIG. 6 is an exploded perspective view of the sampling valve of FIGS. 1A and 1B. There can be seen the five loops 21 to 25. The connection member 1 in this preferred embodiment has the connection channels 121 to 125 in the form of channels hollowed out in the face 10. The ends of the channels are designed to be put into alignment with the orifices of two of the loops 21 to 25 in the face 20 of the sampling member 2 when the valve is in the first position. The channels 121 and 125 are suitable for being connected to the outlet 200, visible in this figure, while the inlet 100 is suitable for being connected either directly to the loop 24 or to the loop 25.

In this example, the connection member carries the dispenser channels 3Xa and 3Xb for each of the loops 21 to 25. These channels 3Xa and 3Xb pass through the connection member 1 and appear, on the outside, in the form of pipes to which it is possible to connect fluid outlets, in particular for reagents, and inside the valve, in the face 10, in the form of orifices that come into alignment with the orifices of the loop 2X in the face 20 when the valve is in the third position.

Figure 7A:
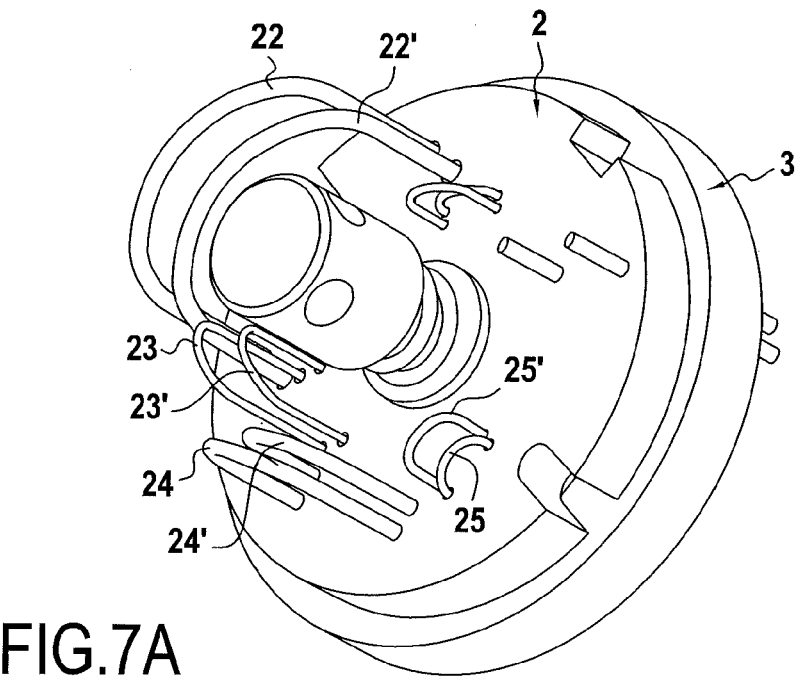
FIGS. 7A and 7B are two perspective views of a variant of the invention.
Figure 7B:
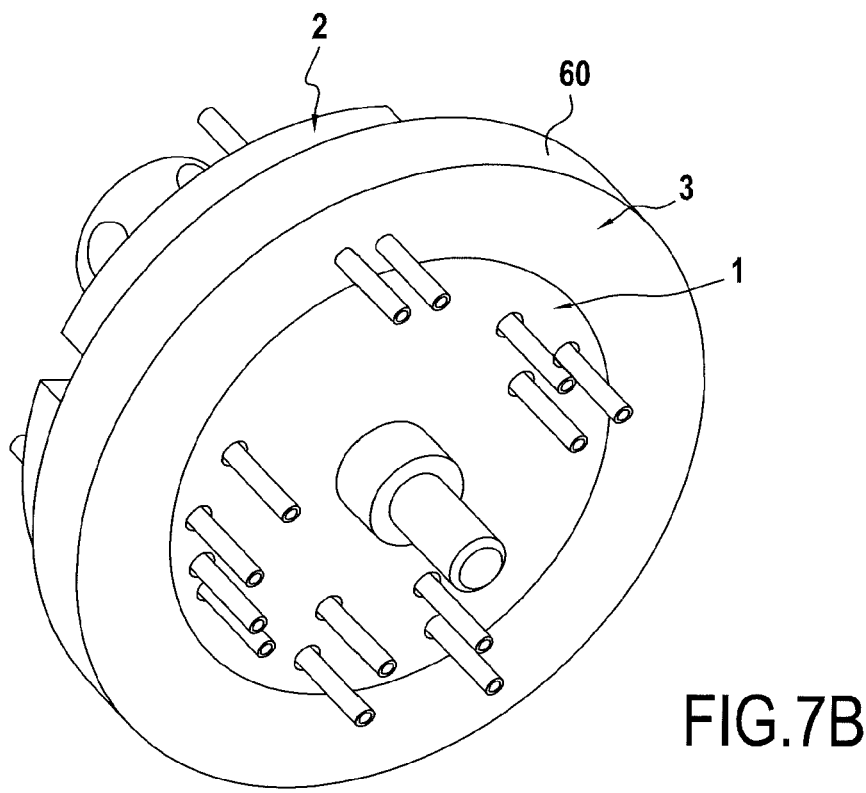

FIG. 7 shows a variant of the invention in which an additional member 3 is added to the sampling valve of the preceding figures and in which the volumes of the loops in each circuit can be modified.

In the variant of FIG. 7, each loop 2X may be duplicated with a duplicate 2X'. These duplicates serve to modify the volumes of the aliquots. Each pair of loops may be connected together via a circuit internal to the sampling member 2 or via a circuit that is internal to the connection member 1, or indeed by a circuit specifically carried by the additional member 3.

This variant with loops of different volumes can be made to have at least one additional position that serves to connect the inlet 100 to standard loops or to loops of different volumes. Provision may thus be made to be able to change the volume of each loop depending on the requirements for analyses.

More precisely, the additional member 3 enables the volumes of the loops to be doubled by taking distinct positions. In the embodiment shown in FIG. 7, it can be seen in FIG. 7B that the connection member 1 is surrounded by the additional member 3 that is in the form of a ring around the connection member 1.

This makes it possible to provide a valve with three members but with only three rectified faces, one on the sampling member 2, one on the connection member 1 coming into contact with the rectified face of the sampling member 2, and a third on the additional member 3, which also comes into contact with the rectified face of the sampling member 2, in the manner shown in FIG. 7.

The presence of the additional member 3 makes it possible in particular to switch between a position in which the collecting tube is accessible ("tube open") and a position in which access to the collecting tube is closed ("tube closed").

In a variant embodiment, in practice independent of the invention, it is possible to release the blood collecting tube even more quickly in the collecting zone.

It is possible to envisage the blood being taken into the collecting tube in a single operation so that the quantity of blood that is required for all of the analyses is then situated immediately after the collecting needle. The tube can then be removed from the collecting zone.

Thereafter, the valve is switched to the first position in order to fill the first loops prior to switching the valve to the second position in order to fill the second circuit.

This implementation amounts to using a tank, that may be no more than a tube on the path of the fluid for analysis, located between the collecting needle and the valve and presenting a volume that corresponds to the total volume of blood needed to fill the five sampling loops.

This implementation presents the advantage of occupying the collecting tube for very little time, thereby releasing it very quickly for any other analyses that might be made using other sampling valves, thus enabling the rate of throughput of the appliance to be further increased.

Finally, it should be observed that various implementations may be performed on the principles of the invention as defined in the following claims.

What is claimed is:

1. A sampling valve for taking a fluid for a plurality of analyses using reagents from a single collecting vessel, said valve comprising two members in contact with each other via respective ones of their faces referred to as "contact" faces, the two members being movable relative to each other, each member having a network of fluid-flow channels, at least some of which open out into the contact face thereof, wherein the network of channels of one of said members, referred to as a so-called sampling member, comprises at least three independent sampling loops, each suitable for containing an aliquot of the fluid, the sampling valve having at least as many reagent-dispenser channels and aliquot-outlet channels as it has loops, the other member, referred to as a so-called connection member, being capable of taking at least three distinct functional positions relative to the sampling member:
- a first position enabling a fluid inlet into the valve to be connected to a first sampling circuit comprising a plurality of sampling loops that are then connected to one another via channels of the network of channels of the connection member that are then specifically in alignment with each of the loops, said first position also serving to connect, via one or more channels of the network of channels of the connection member, at least one loop of a second sampling circuit, having at least one sampling loop, to a reagent-dispenser channel and to an aliquot-outlet channel;
- a second position enabling the fluid inlet to be connected to the second sampling circuit, while, in said second position, at least one sampling loop of the first sampling circuit is isolated from each of the fluid inlet, the reagent-dispenser channels and the aliquot-outlet channels; and
- a third position in which said at least one sampling loop of the first sampling circuit is connected via channels of the network of channels of the connection member to a reagent-dispenser channel and to an aliquot-outlet channel, while, in said third position, said at least one sampling loop of the second sampling circuit is isolated from each of the fluid inlet, the reagent-dispenser channels and the aliquot-outlet channels.

2. A sampling valve according to claim 1, wherein, in the third position, all of the loops of the first circuit are each connected, via channels of the network of channels of the connection member to a respective reagent-dispenser channel and to a respective aliquot-outlet channel.

3. A sampling valve according to claim 1, wherein the connection member is designed to take a third position such that a fraction only of the sampling loops of the first circuit are each connected, via channels of the network of channels of the connection member, to a respective reagent-dispenser channel and to a respective aliquot-outlet channel, and to take at least other functional position such that at least one other distinct fraction of the sampling loops of the first circuit are each connected, via channels of the network of channels of the connection member, to a respective reagent-dispenser channel and to a respective aliquot-outlet channel.

4. A sampling valve according to claim 3, wherein the second position for connecting the fluid inlet to the second sampling circuit is also another functional position such that at least one other fraction of the sampling loops of the first circuit are each connected via channels of the network of channels of the connection member to a respective reagent-dispenser channel and to a respective aliquot-outlet channel.

5. A sampling valve according to claim 3, wherein each of the sampling loop fractions is constituted by a pair of sampling loops.

6. A sampling valve according to claim 3, wherein each sampling loop fractions is constituted by a single sampling valve loop.

7. A sampling valve according to claim 1, wherein the connection member is also a dispenser member carrying the reagent-dispenser channels and the aliquot-outlet channels of the sampling valve.

8. A sampling valve according to claim 1, wherein the sampling member is also a dispenser member carrying the reagent-dispenser channels and the aliquot-outlet channels of the sampling valve.

9. A sampling valve according to claim 1, wherein the members are disks that are movable in rotation relative to each other.

10. A sampling valve according to claim 1, wherein the connection member carries a channel constituting the fluid inlet to the valve.

11. A sampling valve according to claim 1, wherein the sampling member carries a channel constituting the fluid inlet into the valve.

12. A sampling valve according to claim 1, wherein the fluid is a biological fluid and the first circuit is dedicated to routine analyses and the second circuit is dedicated to particular analyses.

13. A fluid analysis appliance implementing at least one sampling valve according to claim 1.

* * * * *